United States Patent [19]

Holtkamp, Sr.

[11] Patent Number: Plant 7,678

[45] Date of Patent: Oct. 15, 1991

[54] AFRICAN VIOLET PLANT NAMED YELLOWSTONE

[76] Inventor: Reinhold Holtkamp, Sr., Blumenstrasse 28, D 4242 Rees-Haffen, Fed. Rep. of Germany

[21] Appl. No.: 551,740

[22] Filed: Jul. 12, 1990

[51] Int. Cl.[5] ..... A01H 5/00

[52] U.S. Cl. ..... Plt./69

[58] Field of Search ..... Plt./69

[56] References Cited

U.S. PATENT DOCUMENTS

P.P. 6,437 12/1988 Holtkamp ..... Plt. 69

*Primary Examiner*—James R. Feyrer

*Attorney, Agent, or Firm*—Foley & Lardner

[57] ABSTRACT

A new and distinct cultivar of African violet named Yellowstone which is a sport of Barbados, disclosed in U.S. Plant Pat. No. 6,437. Yellowstone is characterized by its double, purplish blue flowers with frilled white edges; strong, upright flower stems that curve slightly toward the center to form a bouquet above the leaves; medium green, velvety leaves; profuse flowering, vigorous growth habit, flowering 9–10 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar names Yellowstone.

The new cultivar was referred to during the breeding and selection process by the designation M/H/77/9 and is a port of Barbados, disclosed in my U.S. Plant Pat. No. 6,437. Yellowstone is similar in all essential respects to Barbados except for its double blooms.

Yellowstone was discovered in a flowering block of the parent cultivar Barbados and subseqeuntly selected. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Yellowstone has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Yellowstone, which in combination distinguish this African violet as a new and distinct cultivar:

(1) Strong, upright flower stems curving slightly toward the center.

(2) Purplish blue, double flowers with frilled white edges.

(3) Profuse flowering.

(4) Each plant carries 8–10 and more upright flower stems, each of which carries 6–8 and more flowers.

(5) Long lasting, non-dropping flowers.

(6) Vigorous grower.

(7) First flash of flowers appears 9–10 weeks after potting and forms a tight bouquet above the leaves.

(8) Plant saleable 9 to 10 weeks after potting.

(9) Seed capsules push slightly through.

(10) Medium green, oval, velvety leaves.

(11) After maturity the flowers dry off and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 a.m. in Nashville, Tenn.

Botanical classification: *Saintpaulia ionantha,* Ramat., c.v. Yellowstone.

Parentage: Sport of Barbados, disclosed in U.S. Plant Pat. No. 6,437.

Propagation: The new cultivar holds its distinguishing characteristics through successive propagations by leaf cuttings.

Plant: From 8 cm to 11 cm tall when grown in pots, and approximately 23–27 cm in diameter when fully grown.

Leaves:

*General form.*—Oval.

*Diameter.*—65–70 mm wide and 70–80 mm long.

*Texture.*—Velvety.

*Aspect.*—Hairy, slightly shiny.

*Veins.*—Upperside: visible; underside; well pronounced, light green and shiny; purplish green in between the veins.

*Color (upperside).*—Yellow-Green Group 137 A.

*Color (underside).*—Yellow-Green Group 148 between C and D with touches of Greyed-Purple 186 C.

*Petiole.*—Strong upright, brownish purple, hairy.

Flowers:

*Buds.*—Bell-shaped, 8–10 mm just before opening, purplish blue.

*Sepals.*—Five (5). Color: Green with brownish touch.

*Calyx.*—Shape: Funnel-shaped. Aspect: Spear-shaped, hairy.

*Peduncle.*—Character: Strong upright, hairy. Color: Green with brownish touch.

Individual flowers:

*Size.*—35–40 mm.

*Shape.*—Double with slightly frilled edges.

*Color* (*upperside*).—Violet-Blue Group 93 B with white edges. Under cooler temperature and more intensive lighting, the color tends to intensify.

*Color* (*underside*).—Violet-Blue Group 92 A.

*Borne.*—Each flower stem carries 6–8 and more flowers on strong, upright peduncle that are free standing above the leaves, thereby forming a compact bouquet.

*Flowering habit.*—Flowers 9–10 weeks after potting.

Reproductive organs:

*Stamens.*—Two (2). Anthers: 2 composed of 4 anther cells, seed capsule pushes slightly through.

*Filaments.*—Yellowish green with purplish traces 4–5 mm long.

*Pollen color.*—Yellow Group 7 A.

*Styles.*—6–7 mm long, purplish blue, base of ovary light green and hairy.

Roots: Normally developed, white when young, turning slightly brownish when older.

Disease resistance: Good.

General observations: Yellowstone is a very attractive, vigorous grower having purplish blue, double flowers with frilled white edges. Each of the 8–10 and more flowers stems carries 6–8 and more flowers. The anthers are usually covered up because of the double blooms. The flowers are long-lasting and non-dropping and the seed capsule pushes slightly through. A bouquet of flowers free standing above the medium green, velvety leaves develops after approximately 9–10 weeks.

I claim:

1. A new and distinct cultivar of African violet named Yellowstone, as described and illustrated, and particularly characterized by its double, purplish blue flowers with frilled white edges; strong, upright flower stems that curve slightly toward the center to form a bouquet above the leaves; medium green, velvety leaves; profuse flowering, vigorous growth habit, flowering 9–10 weeks after potting, and its long-lasting and non-dropping flowers.

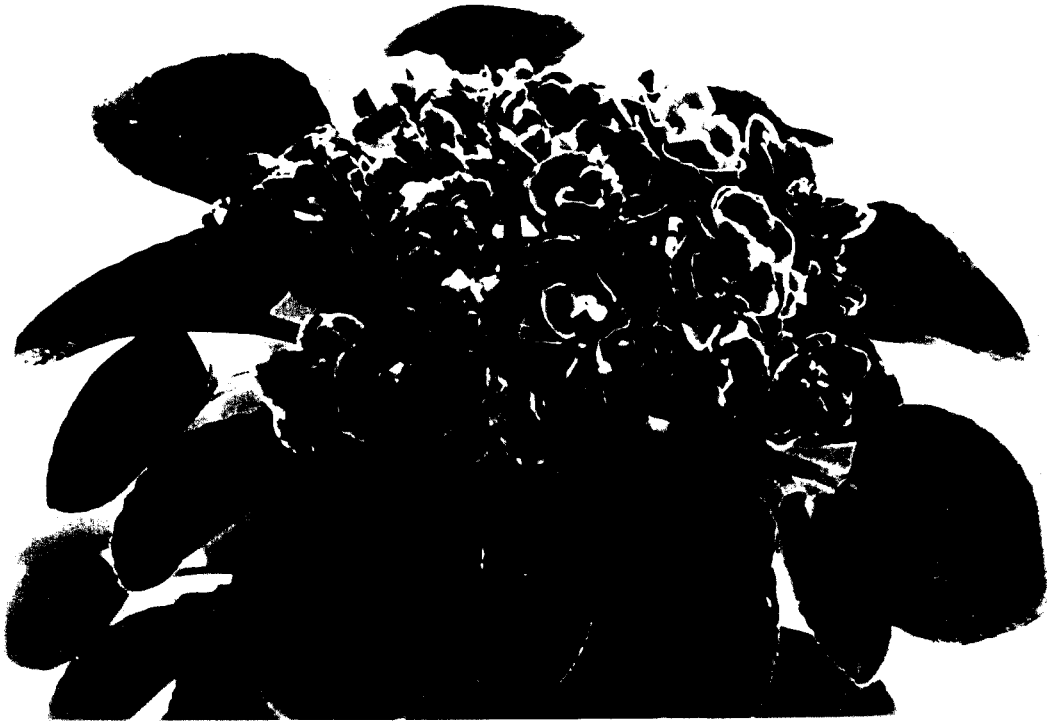

* * * * *